US005902579A

United States Patent [19]

Eisenschink et al.

[11] Patent Number: 5,902,579
[45] Date of Patent: May 11, 1999

[54] NATAMYCIN-CONTAINING STREPTOMYCES BIOMASS AND ITS USE IN ANIMAL FEED

[75] Inventors: Michael Alan Eisenschink, Hoffman Estates, Ill.; James R. Millis, Kohler; Phillip Terry Olson, Manitowoc, both of Wis.; Bruce Dexter King; Mary Ellen Rowland, both of Highland, Ill.

[73] Assignee: Bio-Technical Resources, Manitowoc, Wis.

[21] Appl. No.: 08/639,618

[22] Filed: Apr. 29, 1996

Related U.S. Application Data

[63] Continuation of application No. 08/298,487, Aug. 30, 1994, abandoned, which is a continuation-in-part of application No. 07/826,741, Jan. 28, 1992, abandoned, and a continuation-in-part of application No. 08/262,804, Jun. 20, 1994, Pat. No. 5,686,273, which is a continuation-in-part of application No. 07/997,614, Dec. 23, 1992, abandoned, which is a continuation-in-part of application No. 07/740,545, Aug. 5, 1991, abandoned, and a continuation-in-part of application No. 07/997,613, Dec. 23, 1992, abandoned, which is a continuation-in-part of application No. 07/740,536, Aug. 5, 1991, abandoned, and a continuation-in-part of application No. 08/237,473, May 3, 1994, Pat. No. 5,591,438.

[51] Int. Cl.[6] .............................. A01N 63/00; C12N 1/20
[52] U.S. Cl. ..................... 424/93.43; 435/252.1; 435/253.5; 435/119; 514/31; 536/6.5
[58] Field of Search .................. 435/252.1, 253.5, 435/119; 424/93.43; 514/31; 536/6.5

[56] References Cited

U.S. PATENT DOCUMENTS

| | | |
|---|---|---|
| 3,378,441 | 4/1968 | Bridge . |
| 3,655,396 | 4/1972 | Goto et al. . |
| 3,892,850 | 7/1975 | Struyk . |
| 4,536,494 | 8/1985 | Carter . |
| 4,600,706 | 7/1986 | Carter ............................ 514/31 |
| 4,770,876 | 9/1988 | Bischoff et al. . |
| 5,226,347 | 11/1993 | King . |
| 5,591,438 | 1/1997 | Olson ........................... 424/195.1 |

FOREIGN PATENT DOCUMENTS

| | | |
|---|---|---|
| 669761 | 3/1957 | Canada . |
| 677040 | 7/1957 | Canada . |
| 669761 | 9/1963 | Canada . |
| 677040 | 12/1963 | Canada . |
| 684259 | 4/1964 | Canada . |
| 0 079 707 | 10/1982 | European Pat. Off. . |
| 846933 | 7/1957 | United Kingdom . |
| 0 027 013 | 3/1978 | United Kingdom . |
| 2106498 | 7/1982 | United Kingdom . |
| WO 93/00913 | 1/1993 | WIPO . |
| WO 93/01720 | 2/1993 | WIPO . |

OTHER PUBLICATIONS

"Pimaricin," in *The Merck Index*, 8th Ed., P.g. Stecher, Ed., Merck & Co., 1968, p. 834.

*Primary Examiner*—Irene Marx
*Attorney, Agent, or Firm*—Sheridan Ross P.C.

[57] ABSTRACT

Natamycin biomass comprising 5–60% natamycin, most preferably 25–60% natamycin, and methods for forming the biomass, are disclosed. The natamycin biomass can be mixed with compatible carrier to form a premix comprising 0.2–5% natamycin. The premlix may be mixed with animal feed to form an animal feed mixture comprising cracked grain and 1.1–110 ppm of natamycin.

21 Claims, No Drawings

NATAMYCIN-CONTAINING STREPTOMYCES BIOMASS AND ITS USE IN ANIMAL FEED

CROSS-REFERENCE TO RELATED APPLICATIONS

This application is a continuation of U.S. patent application Ser. No. 08/298,487, filed Aug. 30, 1994, now abandoned, which is a continuation-in-part of U.S. patent application Ser. No. 07/826,741, filed Jan. 28, 1992; now abandoned, and a continuation-in-part of U.S. patent application Ser. No. 08/262,804, filed Jun. 20, 1994, now U.S. Pat. No. 5,686,273, which is a continuation-in-part of U.S. patent application Ser. No. 07/997,614, filed Dec. 23, 1992, now abandoned, which is a continuation-in-part of U.S. application Ser. No. 07/740,545, filed Aug. 5, 1991, now abandoned; and a continuation-in-part of U.S. patent application Ser. No. 07/997,613, filed Dec. 23, 1992 now abandoned, which is a continuation-in-part of U.S. application Ser. No. 07/740,536, filed Aug. 5, 1991, now abandoned; and a continuation-in-part of U.S. patent application Ser. No. 08/237,473, filed May 3, 1994, now U.S. Pat. No. 5,591,438 all of which are incorporated herein by reference.

FIELD OF THE INVENTION

This invention relates natamycin biomass that contains 5–60% natamycin; to methods for preparing the biomass; to animal feed mixtures comprising the natamycin biomass; and to a method for feeding the animal feed mixtures.

BACKGROUND OF THE INVENTION

Natamycin (also known as pimaricin or tenecetin) is a member of the polyene family of antimycotics (Florey, "Analytical Profiles of Drug Substances", Vol. 10, 1981; Merck Index, 8th ed., "Pimaricin", p. 834). Natamycin has been produced in purified form and, in this form, is known to be an effective antifungal agent. Carter, U.S. Pat. Nos. 4,536,494 and 4,600,706, discloses that dry, crystalline natamycin physically mixed with feed grain in effective amounts, prevents fungal mycotoxin contamination of feed. Elliott, Canadian Patent 684,259, discloses feed additives of *Candida albicans* fermentation product, with or without the inclusion of an antifungal agent such as nystatin or pimaricin.

Natamycin is prepared by fermentation, such as disclosed in U.K. Patent 846,933, using *Streptomyces gilvosporeus*. In this process, natamycin is recovered by methanol extraction followed by tedious steps of adsorption and elution. Bridge, U.S. Pat No. 3,378,441, discloses recovery of natamycin by salting it out of the fermentation broth, extracting with methanol, removing the solids, and then evaporating the liquid. Struyk, U.S. Pat. No. 3,892,850, discloses recovery of natamycin by extraction with acidified butanol followed by distillation and precipitation. Each of these processes require an expensive recovery step, such as adsorption and elution, distillation, or evaporation. Consequently, natamycin has not been widely used because of its extremely high cost of manufacture, isolation, and purification. A need exists for a method of using natamycin that does not require an expensive recovery step.

SUMMARY OF THE INVENTION

In one embodiment the invention is natamycin biomass comprising 5–60% natamycin, most preferably 25–60% natamycin. In another embodiment, the invention is an animal feed premix, the premix comprising natamycin biomass and with a compatible carrier, the premix comprising 0.2–5% natamycin. In another embodiment, the invention is an animal feed mixture comprising cracked grain and natamycin biomass; the animal feed mixture comprising 1.1–110 ppm of natamycin.

DETAILED DESCRIPTION OF THE INVENTION

Biomass Production

Inoculum Preparation

Any natamycin producing Streptomyces species can be used to prepare natamycin biomass. A preferred Streptomyces species is *Streptomyces gilvosporeus*. *Streptomyces gilvosporeus* ATCC 13326, a preferred strain, is available from the American Type Culture Collection (ATCC), 12301 Parklawn Drive, Rockville, Md. 20852, USA. Any other natamycin producing organism, such as *Streptomyces chattanogensis*, or *Streptomyces natalensis*, may also be used.

Spores of the natamycin producing organism are germinated to produce an actively growing culture. A sterilized (e.g., autoclaved), agar slant is heavily inoculated with the actively growing culture and incubated until the slant is substantially covered with spores. The spores are scraped into a small amount of a liquid, such as distilled water, nutrient medium, etc., to produce an aqueous spore suspension.

A number of agar slant media can be used to promote sporulation of the culture. Appropriate agar slant media typically comprise at least one of: yeast malt agar, Hickey-Turner agar, GYA agar, Pridham agar, potato dextrose, Bennett's agar, etc. Suitable media are given in the Examples.

The spore suspension typically contains about $10^5$–$10^{10}$ CFU/mL. A high concentration (e.g., $10^8$ CFU/ nL or higher), of viable spores within the spore suspension is preferred. If the concentration of spores is too low, it takes much longer to produce the cell concentration required for cost-effective natamycin production. A lower spore concentration lengthens the propagation time and increases the likelihood of contamination by an unwanted organism. In addition, a low spore concentration may tend to promote the formation of large, tightly packed mycelial pellets. These pellets are unsuitable for obtaining high yields of natamycin due to problems associated with oxygen transfer, mass transfer of nutrients into the pellets, etc. Should the size of mycelial pellets become undesirable, the pellets can be broken apart physically, such as by using a shear force (e.g., blending).

Inoculum Propagation

The aqueous spore suspension is germinated and cell growth continued until the cell density is adequate to be used as an inoculum. A suitable inoculum cell density is about 1–5 g/L (dry weight). The inoculum is used at a volume of about 0.1–10% of the natamycin production medium volume.

The medium used for propagation determines the cell density and the metabolic state of the inoculum. A sufficient amount of protein nitrogen that contains complex growth factors (e.g., vitamins), inorganic elements (e.g., potassium, sodium, calcium, etc.), and trace elements (e.g., boron, cobalt, iron, copper, zinc, etc.) that are commonly present in the protein nitrogen source is needed to produce an inoculum possessing the desired cell density and metabolic state. The protein nitrogen source may be any source that will propagate the spore suspension into an inoculum that will produce the desired high yields of natamycin. Suitable media are given in the Examples.

A source of metabolizable carbon must also be supplied to the medium in an amount sufficient to achieve the desired cell density. For best results, the carbon source should not be completely depleted during propagation. Depletion of the carbon source tends to adversely alter the metabolic state of the inoculum and reduce the yield of natamycin during fermentation.

A suitable medium for inoculum propagation may be prepared in water (e.g., low mineral content water, distilled water, etc.), and comprises: (a) about 2–16 g/L, typically about 8 g/L, of a protein nitrogen source; and (b) a sufficient metabolizable carbon source to avoid total carbon depletion, usually about 5–30 g/L, typically about 15 g/L.

The medium may be prepared by conventional techniques (e.g., separate or simultaneous sterilization of the carbon and nitrogen sources at temperatures of about 120–140° C.). After sterilization, the medium desirably has a pH of about 7. The spore suspension is introduced to the medium and the medium is heated to about 25–40° C., typically, about 28–35° C.

To achieve the large volumes of aqueous inoculum which are desirable for fermentation production of natamycin, several propagation steps are required, each carried out in a volume greater than the previous step. It is advantageous to keep the culture in an exponential growth mode during propagation by increasing the volume of the inoculum during each step of the propagation. This can be done by either minimizing the duration of each step or by minimizing the number of steps. Once the desired cell density has been achieved, the inoculum is transferred to a larger vessel for further growth. The length of time an individual step is permitted to continue depends upon the composition of the medium, quantity of Streptomyces cells desired, temperature, etc. Typically, a propagation step continues for about 6 to 24 hours.

Propagation requires aeration of the inoculum. The vessel or flask housing the inoculum, may be agitated on a rotary shaker at about 200 rpm. or by impeller located within the vessel that houses the inoculum while sterile air is forced into the bottom of the vessel.

Natamycin Biomass Production

The fermentation medium must contain the proper amounts of metabolizable carbon and protein nitrogen. Also, it is desirable that the medium contain complex growth factors (e.g., vitamins), and inorganic elements (e.g., potassium, sodium, calcium, etc.), and trace elements (e.g., boron, cobalt, iron, copper, zinc, etc.), that are commonly present in the protein nitrogen source.

As disclosed in U.S. patent application Ser. No. 08/262, 804, filed Jun. 20, 1994, incorporated herein by reference, a suitable medium for fermentation may be prepared in water (e.g., low mineral content tap water, distilled water, etc.), and comprises: (a) about 80–250 g/L of a metabolizable carbon source; and (b) at least 15 g/L and, normally about 20–80 g/L, of a protein nitrogen source containing a high level of protein and trace ingredients. The protein nitrogen source comprises a non-yeast protein nitrogen component and a yeast protein nitrogen component. These two protein nitrogen components are present in a ratio ranging, respectively, from about 3:1 to 9:1 based on protein content of the components, preferably about 4:1 to 8:1 and more preferably about 5:1 to 7:1.

The non-yeast protein nitrogen component may be supplied from a wide range of sources, such as soy protein products (e.g., isolates, flours, meals, etc.). Desirable natamycin yields are obtained with a soy protein source comprising 80–95% protein. The non-yeast protein nitrogen component may also comprise beef extract, protein hydrolysates (e.g., peptones). The yeast nitrogen component is supplied by yeast protein (e.g., extracts, autolysates, etc.).

The production medium must also include a source of metabolizable carbon. The carbon source may be supplied in any expedient form such as glucose, polysaccharide, corn and potato starches, etc.

It is not necessary to initially add the entire amount of carbon source. An appropriate amount of carbon source may be initially added to the fermentation medium and addition continued after the fermentation has begun. For example, the initial concentration of carbon source may be about 40 g/L. Thereafter, carbon source is added to the fermentor at a rate that will maintain the concentration at or above the minimum level required for fermentation. Typically the concentration is maintained at about 5–30 g/L, more typically about 20 g/L. Toward the end of the fermentation, and after the major fermentation period, carbon source addition is discontinued so that little or no carbon source is left at the end of the fermentation.

The fermentation is carried out in an appropriately sized fermentation vessel. About 0.1–10%, usually about 2%, by volume of inoculum is added to the production medium. The remainder of the volume of the fermentor comprises the fermentation medium. Any technique for introducing the inoculum that delivers the inoculum in an active metabolic state and does not cause contamination of the culture is acceptable. To control foaming it may be desirable to add to the medium 0.01–1% by volume of an anti-foaming agent (e.g., a silicone defoamer).

The fermentation medium is brought to a temperature of about 25–40° C., and normally 28–35° C. The length of time which the fermentation process is allowed to continue depends upon the composition of the fermentation medium, temperature, quantity of cells in the inoculum, quantity of natamycin desired, etc. Typically, the fermentation process is conducted for about 70 to 168 hours.

Oxygen is supplied to the medium during fermentation. It is advantageous to maintain a dissolved oxygen level in the medium of about 20–80% of air saturation during the major portion of the fermentation. The ability to achieve a suitable dissolved oxygen level may be enhanced by proper coordination of the aeration and/or agitation rate. For example, the medium is aerated by forcing sterile air through the medium, usually at a rate of about 0.3–1.0 volumes of air per volume of medium. Although it is generally desirable to agitate the medium during aeration, aeration may produce the desired agitation.

The fermentation generally takes place in three phases. During the first phase, which includes the major portion of cell growth, the concentration of natamycin increases generally exponentially. During the second phase the concentration of natamycin increases linearly with time. Carbon source is added at a rate that will maintain carbon source concentration above the minimum level required for fermentation, typically at or near the rate at which carbon source is being consumed. The third phase is characterized by a plateau in natamycin concentration.

In order to maximize the overall quantity of natamycin that is produced, it is desirable to use a medium and/or an environment that induces the second phase to be rapidly reached and maintained. Natamycin concentrations greater than 5 g/L of natamycin per liter of production medium are produced by this method. Preferably, concentrations greater than about 10 g/L are produced. Natamycin concentrations in excess of 15 g/L have been produced by this method.

Biomass Recovery

During natamycin production, natamycin precipitates out as a free crystals. However, part of the natamycin may also be bound to the cells of the biomass. The natamycin fraction of the dry weight of the biomass is greater than 5%, preferably greater than 10%, more preferably greater than 15%, and even more preferably greater than 25% of the biomass.

At the end of the fermentation natamycin biomass is separated from the fermentation broth. Any solid-liquid separation technique, such as filtration or centrifugation, may be used. Alternatively, the fermentation broth may be concentrated by evaporation so that the resulting concentrate retains all of the valuable nutrients and other ingredients that would be lost in filtration or centrifugation.

After separation from the fermentation broth, the natamycin biomass is dried by any conventional technique, such as by freeze drying, spray drying, fluid bed drying, shelf drying, etc. The temperature used is typically in the range 0–60° C. and depends on the drying technique used and the thermal stability of natamycin within a given technique. Drying and heating renders the biomass non-viable. Typically drying is continued until the biomass contains 15% or less water.

Fermentation processes produce natamycin biomass that contains about 5–35%, preferably 10–35%, more preferably 15–35%, and even more preferably 25–35%, natamycin on a dry weight basis. If desired, the natamycin fraction of the biomass can be increased to about 40–50% by centrifugation, washing with hot water, and drying. Ultrafiltration may be used in place of centrifugation. If the biomass is pretreated with the enzyme lysozyme prior to centrifugation or ultrafiltration, the natamycin fraction of the biomass may be increased to about 60%.

Animal Feed Premix

For convenience, it is desirable to first prepare a concentrated premix of natamycin biomass with a compatible carrier, such as rice hulls, limestone, soybean flour, corn cob fractions, or mixtures thereof. The premix is prepared by mixing the carrier with sufficient natamycin biomass to produce a premix containing about 0.2–5% natamycin. A convenient concentration is 10 g of natamycin per pound of premix (about 2200 ppm). The biomass should be finely divided (particle size less than about 40 $\mu$) so that the natamycin will be evenly distributed in the feed.

Animal Feed Mixtures

The animal feed mixtures comprise animal feed, for example, cracked grain feed for chickens, turkeys, or other poultry, as well as similar feeds for various domestic animals, in combination with a biologically effective amount of natamycin biomass. Trace elements such as boron, cobalt, iron, copper, zinc, manganese, chromium, molybdenum, etc., as well as various vitamins and growth factors, such as riboflavin, may also advantageously be present. Frequently these are provided by commercially available vitamin/mineral supplements. Examples of animal feeds are given in Carter, U.S. Pat. No. 4,600,706, incorporated herein by reference.

This premix is then blended into the final feed, along with other conventional ingredients, to achieve the desired concentration of the natamycin in the feed mixture. Sufficient premix must be added to provide a biologically effective concentration of natamycin in the animal feed mixture. A biologically effective concentration of natamycin inhibits fungal growth in the animal feed mixture and minimizes mycotoxin production. Natamycin also inhibits the growth of yeast. The natamycin should also be effective for a sufficient time, i.e, the time between the preparation of the animal feed mixture and its use. The concentration for natamycin in the feed mixture is typically about 1.1–110 ppm; preferably about 2.2–55 ppm; more preferably 5.5–22 ppm; even more preferably about 8.0–14 ppm. The most preferred concentration is about 11 ppm. If the premix contains 22,000 ppm of natamycin (10 g of natamycin per pound of premix), one pound of premix per ton of feed will produce an animal feed mixture that contains 11 ppm of natamycin. The natamycin biomass should be introduced into the feed before fungal mycotoxin growth commences, or at least before it progresses to an amount detrimental to the health of the animal.

INDUSTRIAL APPLICABILITY

Natamycin biomass inhibits fungal growth and the growth of yeast in animal feeds, particularly grain based feeds. Consequently, for use in animal feed mixtures it is not necessary to extract and purify the natamycin. Not only does the biomass contain biologically effective amounts of natamycin that inhibit fungal contamination of the feed, it also contains significant nutrient values. The biomass can be added to grain based poultry feed, such as feed for broilers, layers, or turkeys, or other grain based feeds, such as feed for swine or cattle.

EXAMPLES

GLOSSARY

| | |
|---|---|
| Profam ® S970 | Isolated soy protein, contains a minimum of 90% protein; Grain Processing Corp., Muscatine, IA |
| Flav-R-Base ™ Type KAT | Primary autolyzed yeast extract, contains about 70% protein; Stauffer Chemical, Westport, CT |

MEDIA

Media were prepared in distilled water and sterilized at 121° C. for about 0.25 hr before use.

Sporulation Medium 1: 4 g/L yeast extract (Difco "Bacto" Yeast Extract); 10 g/L malt extract (Difco Malt Extract); 4 g/L glucose; and 20 g/L agar.

Sporulation Medium 2: 3 g/L yeast extract (Difco "Bacto" Yeast Extract); 3 g/L malt extract (Difco Malt Extract); 5 g/L peptone (Difco "Bacto" peptone); 10 g/L glucose; and 15 g/L agar.

Inoculum Medium 1: 15 g/L glucose; 10 g/L sodium chloride; and 10 g/L peptone (Hormel PSRS peptone).

Inoculum Medium 2: 20 g/L glucose; 10 g/L sodium chloride; 6 g/L corn steep liquor (PPM (brand), Corn Steep Liquid); and 6 g/L peptone (Difco "Bacto" peptone.

Examples 1–4

These examples illustrate production of natamycin by *Streptomyces gilvosporeus* on a medium containing a non-yeast nitrogen component and a yeast nitrogen component in the ratio of about 5.6:1, based on protein content.

Sporulation

*Streptomyces gilvosporeus*, ATCC 13326, was obtained from the American Type Culture Collection as a freeze-dried spore suspension and used as the culture source. The culture was held on the agar slants (Sporulation Medium 1) at about 25° C. until the culture sporulated. The culture sporulated heavily within about 10 days and was used after 14 days.

Spores were scraped off these agar slants into a small amount of inoculum medium (Inoculum Medium 1) so that the spore concentration in the resulting spore suspension was about $10^8$ CFU/mL. Glycerol was added to make the suspension 10% glycerol (volume/volume). The resulting suspension was stored at $-80°$ C. until needed.

Inoculum Propagation

About 1.5 nL of the spore suspension was added to 100 mL of inoculum medium (Inoculum Medium 1) in a 500 mL baffled flask. The inoculum in the baffled flask was incubated for 12 hr at 29° C. and agitated at about 200 rpm on a rotary shaker. About 2 mL of the resulting culture was transferred to 100 mL of inoculum medium and incubation repeated for another 12 hr. About 2 mL of this culture was transferred to 200 mL of medium in a 1 liter baffled flask and the incubation repeated for another 24 hr. This culture was used to inoculate 8 liter of production medium.

Fermentation

The production medium was prepared in distilled water in a 14 liter fermentor and the pH was adjusted to about 7.6 with potassium hydroxide. The fermentor was then sterilized for about 0.25 hr at about 121° C. Glucose was sterilized separately as a 60% solution in distilled water. The composition of the production medium is given in Table 1. The medium also contained 0.05 mL/L defoamer (Mazu, DF 289)

Before inoculation, the production medium was heated to about 29° C. and glucose solution was added to produce an initial glucose concentration of about 40 g/L. An aeration rate of about 0.3 v/v-min. (volumes of air per volume of medium per minute) and an agitation rate of about 300 rpm was established for the fermentor.

Inoculum was added to the fermentation vessel until the medium in the fermentation vessel was about 2% by volume inoculum. After about 40 hr of fermentation, glucose was added at about 1–2 g/L-hr to maintain a glucose concentration of about 20 g/L in the fermentation vessel. The agitation rate was increased as necessary to maintain a dissolved oxygen level of about 50% of air saturation.

An initial volume of about 8.0 liter of production medium was fermented for about 120 hr. Glucose was added as necessary to maintain natamycin production. Up to 230 g/L of glucose was added (Example 4). Natamycin production is indicated in Table 1. The concentration of total solid and the amount of natamycin present in the biomass are indicated in Table 2.

TABLE 1

| Example | Soy Protein[a] (g/L) | Yeast Extract[b] (g/L) | Ratio[c] | Natamycin (g/L) |
|---|---|---|---|---|
| 1 | 19.5 | 4.5 | 5.6 | 8.1 |
| 2 | 26.0 | 6.0 | 5.6 | 10.0 |
| 3 | 32.5 | 7.5 | 5.6 | 12.9 |
| 4 | 39.0 | 9.0 | 5.6 | 15.2 |

[a]Profam ® S970 (minimum of 90% protein)
[b]Flav-R-Base ™ Type KAT (about 70% protein)
[c]Non-yeast protein to yeast protein, corrected for protein content of the extracts.

TABLE 2

| Example | Natamycin (g/L) | Total Suspended Solids (g/L) | Natamycin (%) |
|---|---|---|---|
| 1 | 8.1 | 29.5 | 27.5 |
| 2 | 10.0 | 37.0 | 27.0 |

TABLE 2-continued

| Example | Natamycin (g/L) | Total Suspended Solids (g/L) | Natamycin (%) |
|---|---|---|---|
| 3 | 12.9 | 44.2 | 29.2 |
| 4 | 15.2 | 53.7 | 28.3 |

Example 5

Natamycin fermentation was carried out using *Streptomyces gilvosporeus* ATCC 13326 grown on agar slants, followed by inoculum preparation by further culture growth in the following medium: peptone, 5 g; corn steep liquor, 6 g; sodium chloride, 10 g; glucose, 10 g; and water, 1 L.

The pH was adjusted to 7.0 with potassium hydroxide; the medium was sterilized by heating to 121° C. for 0.25 hr. The culture was incubated at 29° C. on a rotary shaker at 200 rpm for 48 hr. The resulting product was the inoculum for the natamycin production fermentations.

Natamycin production was carried out in a 1-liter fermenter with 600 mL of the following medium: soy protein hydrolysate, 5 g; peptone, 5 g; yeast extract, 3 g; beef extract, 3 g; glucose, 40 g; and water, 1 L.

The pH was adjusted to 7.6 with potassium hydroxide. PPG 2000 was added as a defoaming agent. The medium was sterilized by heating to 121° C. for 0.25 hr. Inoculum (24 mL) was added. Fermentation was carried out at 29° C., 600 rpm agitation rate and 300 mL/min aeration rate. Glucose (18 g) was added during the fermentation. After 161 hr the natamycin concentration was 1.7 g/L and total suspended solids were 19.4 g/L.

Solids were separated from the fermentation broth by centrifugation. The supernate was discarded. The resulting solid was broken up and dried in a fluid bed dryer at 70° C. to a 7% moisture level. A total of 12.5 g of material was recovered of which 8.1% was natamycin.

Example 6

Natamycin production was carried out in a 500 mL baffled flask with 100 mL of medium: soy flour, 23 g; yeast extract, 3 g; glucose, 40 g; and water, 1 L.

The pH was adjusted to 7.6 with potassium hydroxide. The medium was sterilized by heating to 121° C. for 0.25 hr. Inoculum (2 mL) was added to the production medium. Fermentation was carried out at 29° C. on a rotary shaker at 300 rpm agitation rate. Glucose (4 g) was added during the fermentation. After 120 hr the natamycin concentration was 1.3 g/L and total suspended solids were 7.5 g/L.

Solids were separated from the fermentation broth by centrifugation. The supernate was discarded. The resulting solid broken un and dried in a convection oven at 70° C. to a moisture level of 8%. A total of 0.81 g of material was recovered, of which 16% was natamycin.

Example 7

Natamycin production was carried out in a 14-liter fermenter with 8.0 liters of medium: soy flour, 31 g; yeast extract, 3 g; glucose, 40 g; and water, 1 L.

The pH was adjusted to 7.6 with potassium hydroxide. Mazu DF289 was used as a defoaming agent. The medium was sterilized by heating to 121° C. for 0.25 hr. Inoculum (200 mL) was used added. Fermentation was carried out at 29° C., agitation rate 500 rpm, aeration rate 3.0 L/min.

Glucose (480 g) was added during the fermentation (as a 50% solution). After 144 hr the natamycin concentration was 1.26 g/L and total suspended solids were 10.5 g/L.

Solids were separated from the fermentation broth by filtration on a Buchner funnel using Whatman No. 3 filter paper. The filter cake was broken up and dried to 30% moisture in a convection oven at 70° C., and then finally to 6% moisture in a fluid bed dryer. 92 g of material was recovered of which 11% is natamycin.

Example 8

This experiment illustrates inhibition of mold growth in an animal feed mixture that contains natamycin biomass.
Biomass Preparation Two fermentation broths were prepared as described in Example 2. One (9.0 L) contained 9.2 g/L natamycin and 32 g/L total suspended solids (29% natamycin). The other (7.0 L) contained 11.6 g/L natamycin and 36 g/L total suspended solids (36% natamycin). The fermentation broths were combined and a portion (4.0 L) of the mixture centrifuged. The isolated biomass was resuspended in hot water (70° C.) and centrifuged. The resulting biomass was resuspended in hot water, centrifuged, and freeze dried to produce dry biomass that was 44% by weight natamycin.
Biomass Addition to Broiler Feed Commercial crumbled broiler starter chicken feed was ground in a laboratory grinder to a uniform particle size of approximately 0.5 mm. Sterile distilled water was added to increase the moisture content of the feed to 15.5% The feed was divided into two portions. Control feed was untreated. Natamycin biomass was added to the other portion and thoroughly mixed to produce an animal feed mixture that contained 11 ppm of natamycin.

Five 25 g samples of each portion were added to 250 mL wide-mouth Erlenmeyer flasks. Each flask was stoppered with a two-hole rubber stopped. Cumulative oxygen consumption was measured using a modified Micro-Oxymax® respirometer (Columbus Instruments, Columbus, Ohio) using the method generally described in King, PCT 93/24835. Cumulative oxygen consumption has been found to be directly related to microbial growth in feed. Cumulative oxygen consumption as a function of day of incubation is given in the following table.

| CUMULATIVE OXYGEN CONSUMPTION ($\mu L$)[a] | | |
|---|---|---|
| Day of Incubation | No Biomass | Biomass Added |
| Day 1 | 10 | 20 |
| Day 2 | 138 | 132 |
| Day 3 | 278 | 269 |
| Day 4[b] | 429 | 391 |
| Day 5[c] | 6,722 | 2,542 |
| Day 6[d] | 37,493 | 14,888 |

[a]Average of five samples.
[b]$p = 0.1161$
[c]$p = 0.0020$
[d]$p < 0.0001$

Natamycin biomass causes a statistically significant inhibition of mold growth on Day 5 and Day 6 of the experiment.

Example 9

This example illustrates that the fermentation procedure of Example 1 of American Cyanamid, U.K Patent 846,933, produces a low concentration of natamycin.
Sporulation and Inoculum Propagation

*Streptomyces gilvosporeus*, ATCC 13326, was obtained as a freeze-dried spore suspension and used as the culture source. The general procedure of Examples 1–4 was followed to produce a spore suspension which was stored at −80° C. until needed.

About 1.5 mL of the spore suspension was added to 100 mL of inoculum medium (Inoculum Medium 1) in a 500 mL baffled flask. The inoculum in the baffled flask was incubated for 12 hr at 29° C. and agitated at about 200 rpm on a rotary shaker. About 2 mL of the resulting culture was transferred to 100 mL of inoculum medium and incubation repeated for another 12 hr. About 2 mL of this culture was transferred to 200 mL of medium in a 1 L baffled flask and the incubation repeated for another 24 hr.
Fermentation The procedure of Example 1 of American Cyanamid, U.K. Patent 846,933, was generally followed. The production medium was prepared in distilled water in a 14 L fermentor and the pH was adjusted to about 7.6 with potassium hydroxide. The fermentor was then sterilized for about 0.25 hr at about 121° C. Glucose was sterilized separately as a 60% solution in distilled water. The composition of the production medium was about 10 g/L glucose, 2 g/L beef extract, 2 g/L Batco yeast extract, 0.5 g/L asparagine and 0.5 g/L dibasic potassium phosphate. The medium also contained 0.05 mL/L defoamer (Mazu, DF 289)

Before inoculation, the production medium was heated to about 29° C. An aeration rate of about 0.3 v/v-min. (volumes of air per volume of medium per minute) and an agitation rate of about 300 rpm was established for the fermentor.

Inoculum was added to the fermentation vessel until the medium in the fermentation vessel was about 2% by volume inoculum. The agitation rate was increased as necessary to maintain a dissolved oxygen level of about 50% of air saturation. After about 72 hr of fermentation, the concentration of natamycin was about 0.75 g/L.

Having described the invention, we now claim the following and their equivalents.

What is claimed is:

1. A natamycin-containing Streptomyces biomass consisting essentially of:
   (a) cells of Streptomyces selected from the group consisting of *Streptomyces gilvosporeus*, *Streptomyces chattanogensis*, and *Streptomyces natalensis*, and
   (b) natamycin produced by said cells;
      wherein said natamycin produced by said cells constitutes greater than 25% by dry weight of said Streptomyces biomass.

2. The Streptomyces biomass of claim 1 wherein said natamycin produced by said cells constitutes 25%–35% by dry weight of said Streptomyces biomass.

3. A natamycin-containing Streptomyces biomass consisting essentially of:
   (a) cells of Streptomyces selected from the group consisting of *Streptomyces gilvosporeus*, *Streptomyces chattanogensis*, and *Streptomyces natalensis*, and
   (b) natamycin produced by said cells;
      wherein said natamycin produced by said cells constitutes about 40–50% by dry weight of said Streptomyces biomass.

4. An animal feed premix, the premix comprising.
   (a) a natamycin-containing Streptomyces biomass consisting essentially of:
      (i) cells of Streptomyces selected from the group consisting of *Streptomyces gilvosporeus*, *Streptomyces chattanogensis*, and *Streptomyces natalensis*, and (ii) natamycin produced by said cells;

wherein said natamycin produced by said cells constitutes greater than 25% by dry weight of said Streptomyces biomass; and (b) a carrier;

wherein said premix contains 0.2–5% by weight natamycin and said 0.2–5% by weight natamycin was produced entirely by said Streptomyces cells.

5. The premix of claim 4 wherein said carrier is selected from the group consisting of rice hulls, limestone, soybean flour, and corn cob fractions.

6. The premix of claim 4 wherein said premix contains about 2200 ppm of natamycin and said 2200 ppm of natamycin was produced entirely by said Streptomyces cells.

7. The premix of claim 4 wherein said Streptomyces biomass has a particle size of less than about 40µ.

8. The premix of claim 7 wherein said carrier is selected from the group consisting of rice hulls, limestone, soybean flour, and corn cob fractions.

9. The premix of claim 4 in which said natamycin produced by said cells constitutes 25–60% by dry weight of said Streptomyces biomass.

10. The premix of claim 9 in which said Streptomyces biomass has a particle size of less than about 40µ.

11. The premix of claim 10 in which the carrier is selected from the group consisting of rice hulls, limestone, soybean flour, and corn cob fractions.

12. An animal feed mixture comprising:

(a) cracked grain; and (b) natamycin-containing Streptomyces biomass consisting essentially of:

(i) cells of Streptomyces selected from the group consisting of *Streptomyces gilvosporeus, Streptomyces chattanogensis,* and *Streptomyces natalensis,* and (ii) natamycin produced by said cells;

wherein said natamycin produced by said cells constitutes greater than 25% by dry weight of said Streptomyces biomass;

wherein said animal feed mixture comprises 1.1–110 ppm natamycin and said 1.1–110 ppm natamycin was produced entirely by said Streptomyces cells.

13. The feed mixture of claim 12 in which said Streptomyces biomass has a particle size of less than about 40µ.

14. The feed mixture of claim 12 wherein said feed mixture contains about 2.2–55 ppm natamycin and said 2.2–55 pp of natamycin was produced entirely by said Streptomyces cells.

15. The feed mixture of claim 14 in which said Streptomyces biomass has a particle size of less than about 40µ.

16. The feed mixture of claim 12 wherein said feed mixture contains 5.5–22 ppm natamycin and said 5.5–22 ppm of nataycin was produced entirely by said Streptomyces cells.

17. The feed mixture of claim 16 in which said natamycin produced by said cells constitutes 25–60% by dry weight of said Streptomyces biomass.

18. The feed mixture of claim 17 in which said Streptomyces biomass has a particle size of less than about 40µ.

19. The feed mixture of claim 18 wherein said feed mixture contains about 8–14 ppm natamycin and said 8–14 ppm of natamycin was produced entirely by said Streptomyces cells.

20. A natamycin-containing Streptomyces biomass consisting essentially of:

(a) cells of Streptomyces having all of the identifying characteristics of *Streptomyces gilvosporeus* ATCC 13326 and (b) natamycin produced by said cells;

wherein said natamycin produced by said cells constitutes greater than 25% by dry weight of said Streptomyces biomass.

21. An animal feed premix, the premix comprising:

(a) a natamycin-containing Streptomyces biomass consisting essentially of:

(i) cells of Streptomyces having all of the identifying characteristics of *Streptomyces gilvosporeus* ATCC 13326 and (ii) natamycin produced by said cells;

wherein said natamycin produced by said cells constitutes greater than 25% by dry weight of said Streptomyces biomass; and (b) a carrier, wherein said premix comprises 0.2–5% by weight natamycin and said 0.2–5% by weight natamycin was produced entirely by said Streptomyces cells.

* * * * *